United States Patent
Shofner et al.

(10) Patent No.: US 6,532,798 B1
(45) Date of Patent: Mar. 18, 2003

(54) MICRONAIRE, MATURITY AND FINENESS MEASUREMENTS VIA CONTINUOUS COMPRESSION AIR FLOW PERMEABILITY MEASUREMENTS

(75) Inventors: Frederick M. Shofner, Knoxville, TN (US); Christopher K. Shofner, Knoxville, TN (US)

(73) Assignee: Shofner Engineering Associates, Inc., Knoxville, TN (US)

( * ) Notice: Subject to any disclaimer, the term of this patent is extended or adjusted under 35 U.S.C. 154(b) by 0 days.

(21) Appl. No.: 09/663,503

(22) Filed: Sep. 15, 2000

Related U.S. Application Data

(60) Provisional application No. 60/154,527, filed on Sep. 16, 1999, provisional application No. 60/182,731, filed on Feb. 15, 2000, and provisional application No. 60/221,104, filed on Jul. 27, 2000.

(51) Int. Cl.[7] .............................................. G01N 15/08
(52) U.S. Cl. ........................................................ 73/38
(58) Field of Search ........................... 73/38, 37.5, 160, 73/823

(56) References Cited

U.S. PATENT DOCUMENTS

| | | | | |
|---|---|---|---|---|
| 3,065,629 A | * | 11/1962 | Neil ............................... | 73/38 |
| 4,891,967 A | * | 1/1990 | Vogt ............................... | 73/38 |
| 5,359,880 A | | 11/1994 | Elam et al. ..................... | 73/38 |
| 5,427,156 A | | 6/1995 | Saito ....................... | 139/420 B |
| 5,469,253 A | * | 11/1995 | Shofner et al. ................ | 73/160 |
| 5,892,142 A | | 4/1999 | Ghorashi et al. ............... | 73/38 |
| 5,907,394 A | | 5/1999 | Ghorashi et al. .............. | 73/160 |
| 5,943,907 A | | 8/1999 | Ghorashi et al. .............. | 73/160 |
| 6,098,454 A | | 8/2000 | Ghorashi et al. .............. | 73/160 |
| 6,112,131 A | | 8/2000 | Ghorashi et al. ........... | 700/142 |
| 6,161,441 A | * | 12/2000 | Ghorashi et al. .............. | 73/160 |

* cited by examiner

*Primary Examiner*—Hezron Williams
*Assistant Examiner*—Michael Cygan
(74) *Attorney, Agent, or Firm*—Carter & Schnedler, P.A.

(57) ABSTRACT

Instruments for measuring the gas flow permeability of a fiber sample, particularly a cotton fiber sample; and apparatus and methods employing multiple volumetric compressions to acquire data products for determining "micronaire," "maturity" and "fineness" of the fiber sample. A gas flow permeability testing instrument includes sensors in a gas flow stream enabling the determination of fiber mass delivered to a testing chamber, and a computer outputting a control signal to terminate delivery of fibers to the testing chamber when a predetermined mass set point is reached. A multiple-compression fiber gas flow permeability testing device includes a testing chamber into which a fiber sample of known mass is delivered. A movable chamber wall is driven in a substantially continuous manner so as to compress the fiber sample, while a gas flow system determines permeability. A data processing device acquires permeability and chamber wall position (testing chamber volume) data at a sampling rate while the wall is moving.

8 Claims, 7 Drawing Sheets

US 6,532,798 B1

MICRONAIRE, MATURITY AND FINENESS MEASUREMENTS VIA CONTINUOUS COMPRESSION AIR FLOW PERMEABILITY MEASUREMENTS

CROSS-REFERENCE TO PROVISIONAL PATENT APPLICATIONS

The benefit of U.S. Provisional Patent Application Ser. No. 60/154,527, filed Sep. 16, 1999; Ser. No. 60/182,731, filed Feb. 15, 2000; and Ser. No. 60/221,104, filed Jul. 27, 2000 is claimed.

BACKGROUND OF THE INVENTION

The invention relates generally to fiber quality measurements for cotton classing and, more particularly, to air flow permeability instrument measurements.

Cotton standards are supported by the United States Department of Agriculture (USDA) through its Agricultural Marketing Service (AMS). Cotton standards, and the corresponding classing of cotton, are of great importance in determining the market value of a particular bale of cotton, as well as determining suitability of a particular bale of cotton from a gin for subsequent processing at a particular mill in view of the products and processes of that mill. AMS is responsible for preparing and maintaining such cotton standards and does so in its Standards Section located in Memphis, Tenn.

In 1923, the United States and nine European countries entered into the Universal Cotton Standards Agreement. From that time, up until approximately 1965, USDA/AMS cotton classing "measurements" based on the Universal Standards were made entirely by humans. The human measurements included "grade," "extraneous matter" (such as bark and grass), "preparation" (which relates to smoothness of the sample) and "staple length" (long fiber content). Instrument-based cotton classing was introduced in 1965, beginning with micronaire, an air flow permeability measurement, followed in 1980 by High Volume Instruments (HVI), which added measurements of length and strength. HVIs currently measure the fiber qualities of Micronaire, Length, Strength, Color and Trash.

Since approximately 1950, various forms of the "Micronaire" air flow permeability measurement have been widely used in the classification of cotton. The permeability measurement was originally calibrated in terms of linear density or fineness, with dimensions in the United States of micrograms per inch, with a typical and good value being 4 µg/in (10 µg/cm), and with ranges in value from as low as 2 µg/in (5 µg/cm) to as high as 7 µg/in (18 µg/cm). Most varieties, when "normally matured," have values in the range of 3 µg/in (7.6 µg/cm) to 5 µg/in (12.7 µg/cm). It was later found that this fineness interpretation was incorrect, since the calibration between permeability and true weight fineness could not be robustly adjusted to fit most cotton types, so the fineness dimensions were dropped. But since the measurement was found to be useful for processing, particularly for "wastiness" and for other processing problems, the measurement was standardized and its use grew. Micronaire became the first non-human based measurement to enter the trading of cotton, widely, and was introduced officially into AMS classing in 1965.

In the standardization of this simple measurement, a known (by a precision balance) sample mass is compressed into a known, fixed volume, air is forced through this compressed plug, and the resulting air flow permeability, a ratio of flow rate to pressure differential (usually to the one half power), is calibrated in terms of "accepted" values of micronaire provided by the USDA. Thus the measurement is calibrated on cotton at a fixed bulk density of the plug or, alternatively stated, at a fixed compression volume for the fixed and known mass. Nearly 50 years of experience with this measurement substantiate its usefulness but, equally strongly, its shortcomings. Other apparatus has been offered which provides permeabilities at two compressions of the same sample mass. From these data, additional fiber properties, including Maturity and Fineness, can be inferred, based on calibrations for these fiber qualities. These "double compression" testers were manufactured by Shirley Developments, Manchester, England and Spinlab, Knoxville, Tenn., and called the Fineness and Maturity Tester and the Arealometer, respectively. These instruments are not widely used because the calibrations are not sufficiently robust and the results are very operator and sample state sensitive. The Arealometer is no longer manufactured.

Further adding to the difficulties for these measurements, definitions for Maturity and Fineness are not widely agreed. The better or "more unbiased" of the many definitions in use relate to the fiber cross sectional shape and to the fiber cross sectional area, respectively. Such data can only be produced by image analysis of carefully prepared fiber cross sections that are too slow for commercial use, even with modern image analysis methods.

SUMMARY OF THE INVENTION

The better basic definitions referred to above require far more rigorous permeability data; permeabilities at tens of compressions are needed, not two. Prior art apparatus is completely inapplicable for extension to acquire permeability readings from tens of compressions. For clarity, we note that the conventional term "compression" means, more rigorously, bulk density, mass of fiber per unit volume, grams/cm$^3$.

It is therefore seen to be desirable to provide continuous or nearly continuous measurements of rigorous air flow permeabilities, so that robust and useful measurements of cotton Micronaire, Maturity and Fineness can be inferred. It is further seen to be desirable to enable more rigorous calibrations, in terms of basic cross sectional data.

Embodiments of the invention employ sensors to determine when a predetermined mass of fibers has been delivered to a testing chamber, allowing for automated operation without requiring an operator to guess sample weight. The testing chamber has a movable wall, and an actuator drives the movable wall so as to compress the fiber sample in a substantially continuous manner. A transducer measures the position of the movable wall, and a data processing device acquires gas flow rate through the chamber, pressure difference, and position data at a sampling rate while the wall is moving.

DETAILED DESCRIPTION

Figure 1:
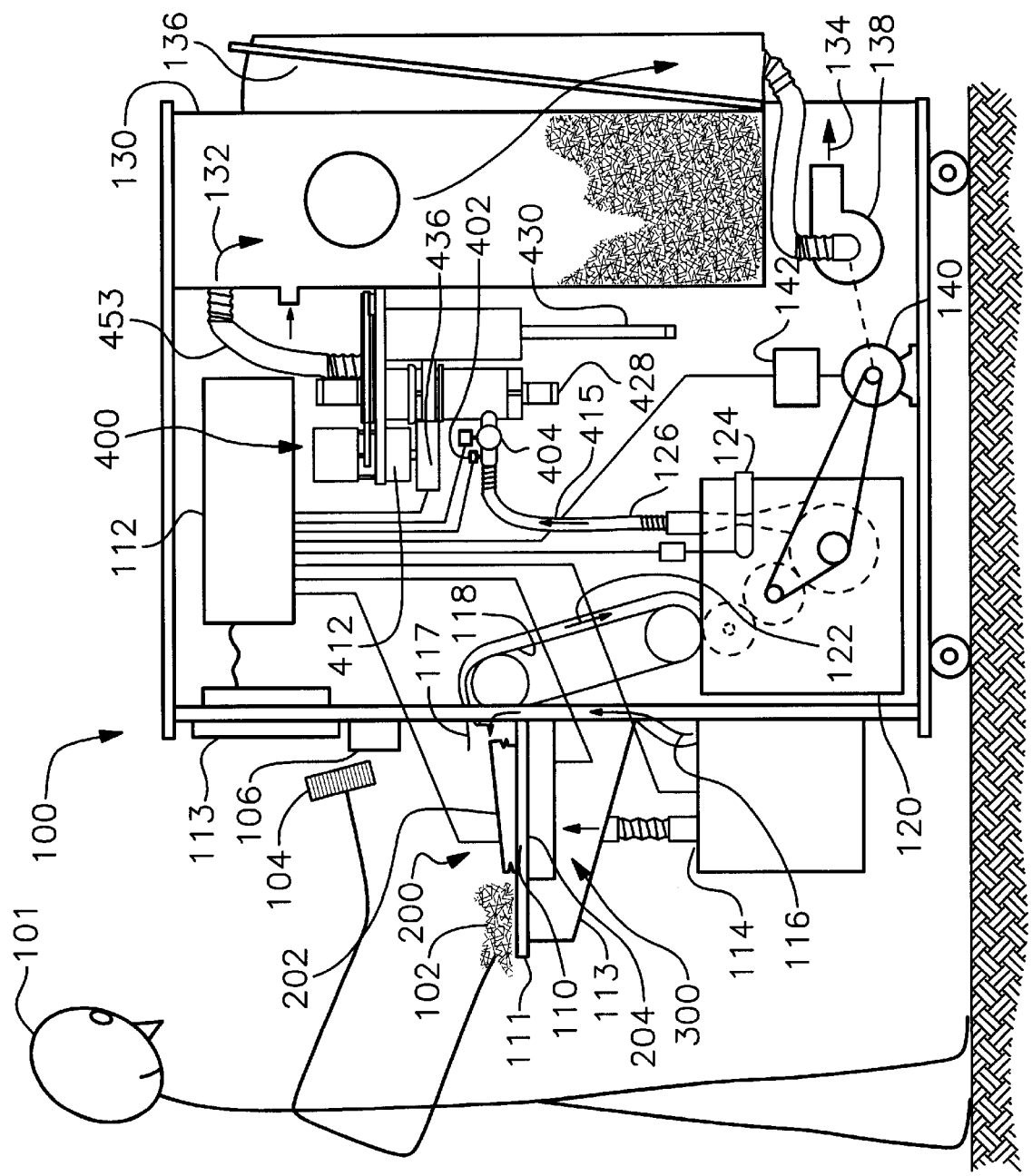
FIG. 1 is an overview of a machine embodying the invention, which machine measures cotton samples to produce multiple data products, including images, and additionally internally and ultra-rapidly conditions samples.

Referring first to FIG. 1, the invention is embodied in a stand-alone instrument 100 which measures cotton samples to produce multiple data products, including images, and additionally internally and ultra-rapidly conditions samples. Instrument 100 is a robust, stand-alone platform upon which fiber quality measurement modules are placed to effect generation of multiple data products. By including internal, ultra-rapid sample conditioning, the instrument 100 eliminates the need for expensive conditioned laboratory space. The machine 100 thus does the work of several other instruments and an expensive laboratory air conditioning system, and does that work in the challenging ginning environment.

System Overview

Operator 101 in FIG. 1 selects a "Classer's Sample" having an estimated weight of approximately 15 grams of sample 102. Such a 15-gram sample is typically 5 inches (12.7 cm) wide×8 inches (20.32 cm) long×1 inch (2.54 cm) thick, when uncompressed. The operator "swipes" permanent bale identification (PBI) tag 104 through bar code reader 106, and prepares and introduces sample 102 into recessed conditioning/test chamber 110 of "stable table" top 111, when pressure/distribution plate 202 is retracted. The operator 101 then initiates automatic conditioning/testing by causing pressure/distribution plate 202 to move over sample 102 in the recessed conditioning/testing chamber 110, compressing the sample to a thickness of less than 3 mm. Directed by a process control computer 112, the machine 100 then automatically effects "Ultra-Rapid Conditioning" in module 200, and additionally effects testing of the sample 102 for Color and Trash in module 300. (Operator 101 can monitor and control the progress of conditioning/testing, and of all other operations, as well as examine the data products produced, stored, and communicated by system 100 via computer 112 and touch-screen display 113.)

Conditioned gas for conditioning sample 102 in conditioning/testing chamber 110 and for transporting and processing sample 102 in subsequent steps is provided by air conditioning module 114. Air conditioning module 114 provides a conditioned gas flow 116 having controlled environmental parameters such as Relative Humidity of 65%, dry bulb Temperature of 70° F. (21° C.), and flow rates of 200 CFM (5.7 m$^3$/min). Conditioned gas flow 116 is conducted to the entrance 117 for both the individualizer 120 flow 122 and for the sample conditioning module 200. In a variation, gas flow 116 is split into two components, one having the fixed, standard parameters just described and a second having variable humidity, temperature, flow rate and pressure and which variable parameters are automatically controlled by a separate controller within air conditioner 114, and which parameter values are determined in accordance with optimally conditioning sample 102 within conditioning/testing chamber 110.

In overview, sample 102, having been manually or automatically placed in recessed conditioning/testing chamber 110, with the pressure/distribution plate assembly 202 over it, is ultra-rapidly "conditioned" from above window 204 and "tested" for Color and Trash below it. Sample 102 may also be tested for moisture content in chamber 110, according to which data air conditioning module 114 is caused to optimally condition sample 102 under control of computer 112.

At the completion of the conditioning/testing cycle, pressure/distribution cover 202 (or pressure plate (not shown) in the event Ultra-Rapid Conditioning is not employed) is opened. The cover 202 may be opened manually, or automatically upon receipt of a signal from computer 112. Sample 102, which is now conditioned for further processing and testing, is automatically or manually moved onto belt 118 for quick transport to an individualizer 120, which thoroughly opens, i.e., "individualizes," sample 102 into its various constituent entities, fibers, neps, trash, seed coat fragments, sticky points, microdust, and the like. A suitable individualizer is disclosed in Shofner et al U.S. Pat. No. 5,890,264. An alternative is for individualizer 120 to also clean sample 102 by removing trash, microdust and other foreign matter. However, in the disclosed embodiment almost all of the individualized entities are transported in the same transport flow stream.

This processing by individualizer 120 causes the thoroughly individualized entities to be entrained in or transported by about 120 CFM (3.4 m$^3$/min) of conditioned air flow 122 such that the fiber and other entity concentrations transported by the gas flow at the output 126 of individualizer 120 are very low. Accordingly, the Nep content of thus-individualized sample 102 is measured with a nep sensor 124 which advantageously is built into the individualizer 120. A suitable nep sensor 124 is as disclosed in Shofner et al U.S. Pat. No. 5,929,460.

Sample 102, whose mass was guessed by operator 101 at approximately 15 grams, is at the output 126 of individualizer 120 in a highly opened, individualized state that simulates the state of fiber in important textile processing machines, especially carding. Accordingly, the state of the fiber is ideal for testing the individual fibers and other entities in the gas flow 122. One such test is the Nep test made by nep sensor 124. Other tests are Micronaire-Maturity-Fineness (MMF), effected by module 400. For Neps and for MMF, it is required that the sample weight be known, not guessed, and sample masses of nominally ten grams are commonly used for both tests. The sample mass can be determined prior to or after the testing using known analytical balance technologies. Post testing weighing can be automated.

The system aspects of the disclosed embodiment can be summarized:

1. Common flow;
2. Optimal sequence for sample tests, from surface measurement of Color and Trash to volume or weight measurements of Neps and Micronaire based on guessed weight or on precise weight;
3. Ideal sample state for simulations of actual processing (e.g., cleanability, processability, spinnability); and
4. Automatic except for selecting and introducing classer's sample, thus eliminating operator effort and errors. System and methods can be extended to complete automation.

Electro-optical Sample Weight Control

Included are a volumetric flow rate sensor 402 and an electro-optional light scattering or extinction sensor 404. Volumetric flow rate sensors 402 are well known, including sensor systems 402 that communicate bi-directionally with computer 112 (RS 232).

The output of electro-optical sensor 404 is proportional to the mass concentration of entities in the gas stream at the output of individualizer 120. Such mass concentration sensors are available from ppm, Inc, Knoxville, Tenn. Note that the volumetric flow rate 415 measured by sensor 402 is preferably (but not necessarily) substantially identical with the flow 122 at the input to individualizer 120, which is also the same as that drawn in at inlet 117, which inflow is a major component of conditioned flow 116 from conditioning apparatus 114. The commonality of the sample 102 conditioning and transport flow, from introduction onto belt 118 to disposal into lint box 130, is one of the major system aspects of the disclosed embodiment.

Since the volumetric flow, $m^3$/sec, via sensor 402, is known, and since sensor 404 measures mass concentration, $g/m^3$, it follows that the product is a measure of the mass delivery rate, $dM_e/dt$ grams/sec. The subscript e indicates that the mass is measured electro-optically. Computer 112 records, at high scan rates of order 100/sec, the outputs of volumetric flow rate sensor 402 and electro-optical mass concentration sensor 404, computes their product, and accumulates the mass delivery rate contributions until a mass set point $M_eSP$, grams, is reached. (This will be recognized as a discrete summation whose limit is the integral of the mass concentration×flow rate product with respect to time.) When this set point is reached, at least two control actions are taken by computer 112: the nep counts and size distribution accumulated during the processing of $M_e$ grams of fiber are stored in a register for later computations, and the fiber is diverted within MMF module 400 to lint box 130. Computer 112 may also speed up the feed rate for the remaining portion of sample 102 since it is of no further use in this context, as a third action.

Deriving a precisely measured sample mass is another of the major system aspects of the disclosed embodiment.

The nep data product is thus neps per gram, which can be based on either the electro-optical value $M_eSP$ just described or a post-determined gravimetric value $M_g$ described in greater detail below in the context of the MMF module 400. Nep size distribution is also provided. Importantly, the sample mass introduced into the MMF module 400 is known, as $M_eSP$, and is far more precise than operator guesswork, having Coefficient of Variation CV typically well under 10. For some applications, the precision of an electronic balance, gravimetric determination, known as $M_g$, including the automated method following the MMF measurement step disclosed below, is not necessary.

The nominally 10 gram portion of sample 102 $M_{esp}$ is then tested in MMF module 400. The remaining portion of the 15 gram estimate has been diverted to lint box 130. After testing, the nominal 10 gram portion is released onto balance 436, where mass $M_g$ is gravimetrically measured and reported to computer 112. Mass $M_g$ can thus be used for all data products requiring precise mass, such as neps/gram, or to adjust MMF readings to the standard 10 gram values. It is very important to note, as another system aspect, that the operator 101 has been freed from the time-consuming and error-prone task of pre-weighing samples 102.

When the balance 436 acquires the sample mass and computer 112 accepts it, computer 112 causes the sample on balance pan 412 to be drawn into suction tube 450 by opening door 452 (FIG. 3) which finally delivers this portion of the sample to lint box 130 via pipe 453. The flow 132 into lint box 130 is the same, preferably, as flows at the inlet to the individualizer 122 and elsewhere, except for short intervals of order one second when neither measurements nor transports are taking place. The flow 134 out of the lint box 130 is not the same, since other flows enter the lint box.

Filter 136, blower 138 having suctions of tens of inches water column at 150 CFM (4.2 $m^3$/min), and motor 140 of about two HP are well known in the art. Note that motor 140 is driven by a variable speed inverter 142 which is controlled by computer 112. Among other control parameters, system suction is maintained constant by use of the variable speed control of motor 140.

Micronaire, Maturity and Fineness Via Continuous Compression Air Flow Permeability Measurements FIGS. 2, 3, 4, 5 and 6 show continuous compression air flow permeability measurement apparatus 400 comprising turntable 401 which rotates above baseplate 403 and is driven by gearmotor 406 via gearbelt 408. Gearmotor 406 is controlled by computer 112 via controller 407 and moves between two primary positions, "Load/Measure" (FIG. 2) and "Transfer/Eject" (FIG. 5), established by microswitches 410, 412. While rotating between these primary positions, turntable 401 is lifted above baseplate 403 by sealing cylinder 411 by just enough clearance (about 0.04 inch (1 mm)) to allow free rotation, without damage to various seals (not shown). When turntable 401 is at one of the primary positions, cylinder 411 drives turntable 401 toward baseplate 403 and compresses the seals and holds it in position for other operations, including the continuous compression of the "plug," which involves forces up to 200 pounds (90 kilogram-force).

On turntable 401 are two diametrically opposite compression/measurement chambers 405A and 405B which enable parallel testing a first sample 102 while loading a second such sample 102. Compression chambers 405A, 405B have approximately one hundred small perforations (FIGS. 2 and 5), having hole diameters of about 0.07 inch (1.8 mm), through which measurement and eject air components flow. Compression chambers 405A and 405B are cylinders, closed at one end, with perforations in the cylindrical walls and endwalls. Sample handling is described first below, followed by a description continuous compression permeability measurements.

Figure 4:
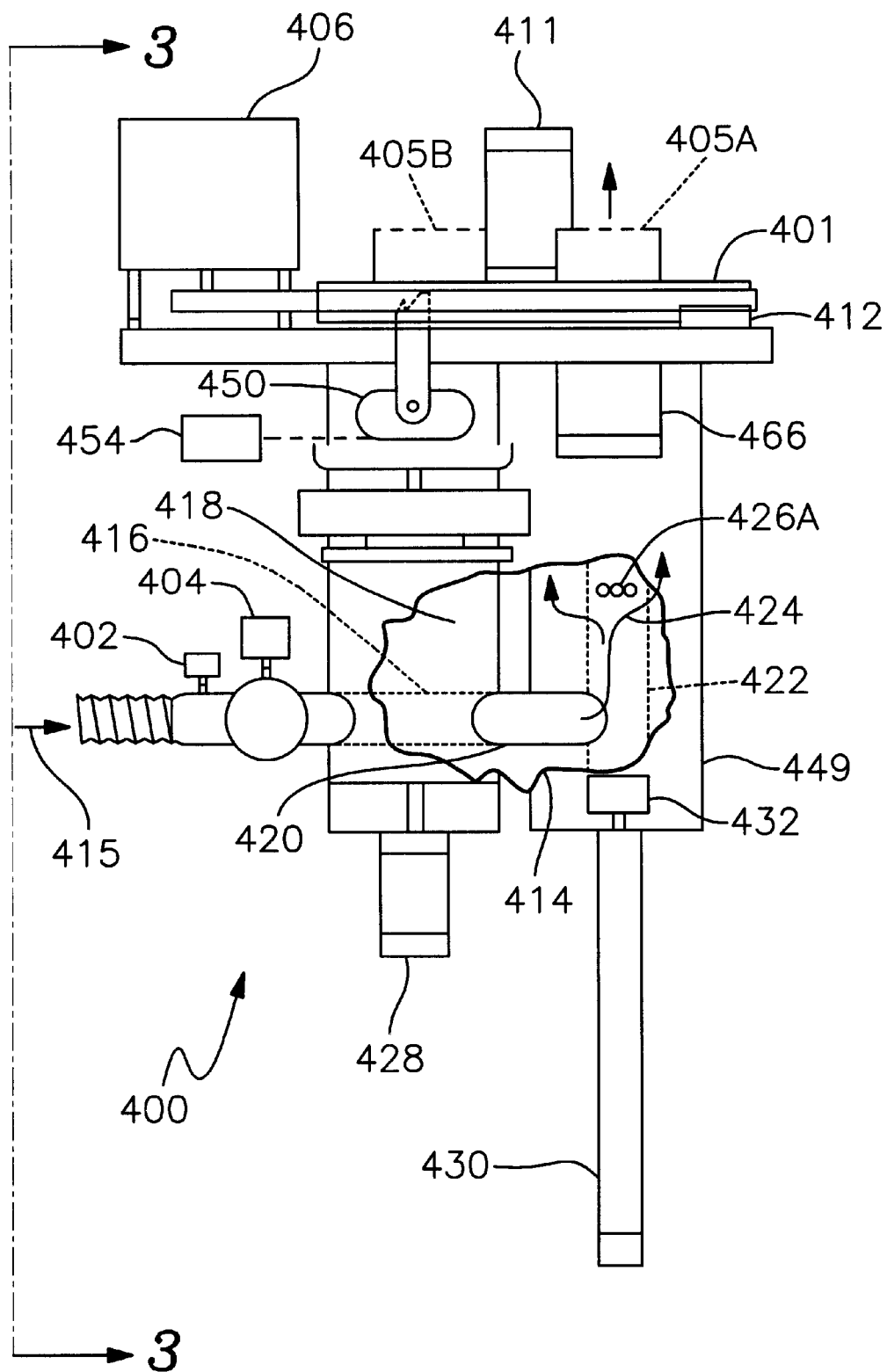
FIG. 4 is an enlarged view of a portion of the FIG. 1 machine, showing the MMF module in side elevation.

FIG. 4 is a larger scale view of FIG. 1 showing only the MMF module 400 in side view. Described hereinabove, in the systems section, is the manner in which operator 101 guesses at 15 gram sample 102 weight, which sample 102 is then conditioned and tested for Color and Trash, delivered by belt 118 to individualizer 120, and then arrives at the input of MMF module 400 in an ideal state for permeability testing, except for the guessed weight. Precisely measured mass is essential for rigorous permeability measurements required for Micronaire, Maturity and Fineness, MMF. Use of air flow rate sensor 402 and mass concentration sensor 404, manufactured by PPM Inc., Knoxville, Tenn., enables the determination of mass flow rate into module 400 and how, upon reaching a mass set point $M_{esp}$, the MMF module 400 internally bypasses the excess part of guessed-weight sample 102. Described next below is how this bypassing is handled internally to MMF module 400, as well as the movement between the two primary positions for compression chambers 405A and 405B.

Referring first to FIG. 4, it can be seen through cutaway section 414 that the two component flow 415, comprised of air and individualized entities from samples 102, and arriving at the input of MMF module 400 from the output of individualizer 120, enters a hole 416 in valve body 418, and is conducted via solid conduit 420 into perforated conduit 422, wherein the individualized entities are separated. Air 424 moves through the entities and through the perforations in conduit 422 into a negative plenum that connects internally to suction conduit 453 (FIG. 3) which in turn connects to lint box 130. The entities 426A from original sample 102 remain within the interior of conduit 422. Upon reaching the mass set point $M_{esp}$, as determined by computer 112 in step-wise summation response to volumetric flow rate sensor 402 and electro-optical mass concentration sensor 404, valve body 418 is pulled down by air cylinder 428 such that the remaining portion of the guessed weight sample 102 is bypassed to lint box 130 and loading cylinder 449 is isolated. We refer to this portion of original sample 102, which achieved the desired mass set point, within narrower tolerances than operator guesswork, as 426A through 426D, as it progresses through the MMF module 400.

Figure 2:
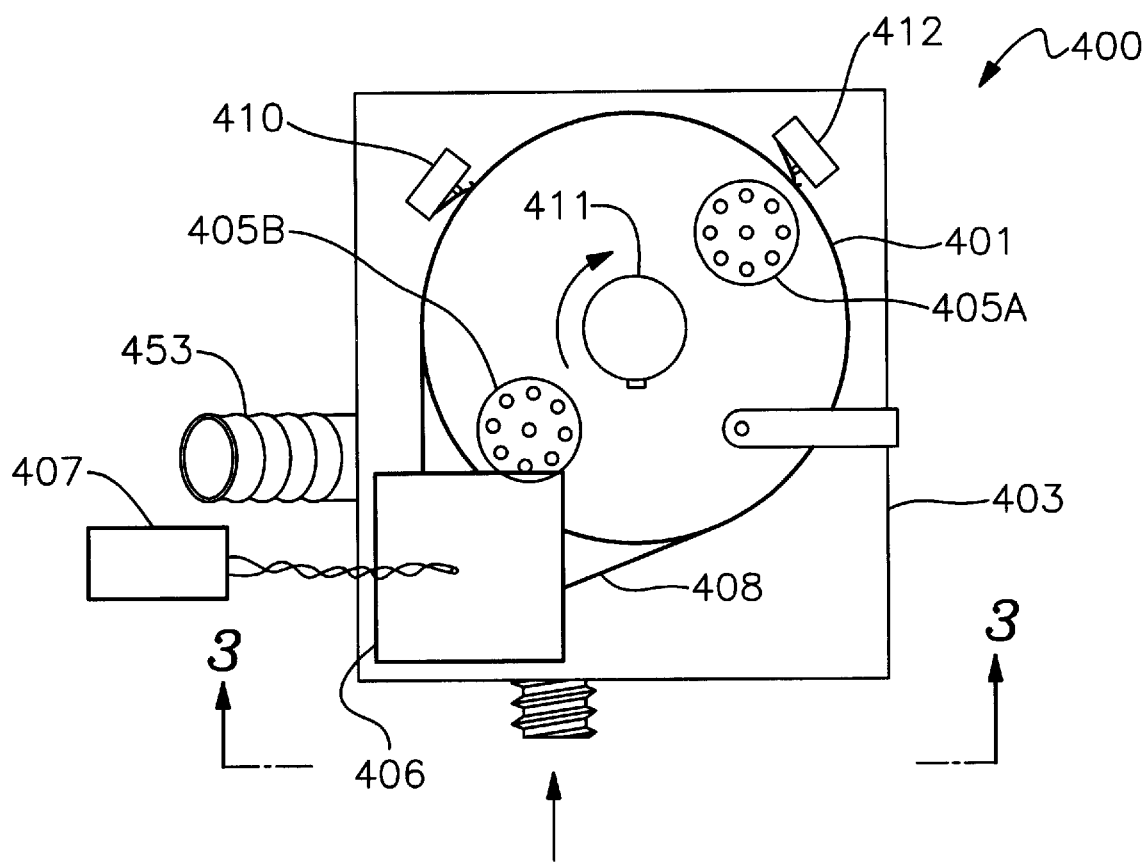
FIG. 2 shows the turntable in its loading/measurement position.

As soon as the longer duration of either achieving the predetermined entity set point mass 426A in perforated conduit 422 or as soon as the permeability measurement taking place in 405A is finished (see below), turntable 401 is slightly lifted by sealing cylinder 411 and rotates clockwise from the "Loading/Measurement" position seen in FIG. 2 to the "Transfer/Eject" position seen in FIG. 5. In FIG. 2, compression chamber 405A is in the "Measurement" position while chamber 405B is in the "Loading" position. There is no corresponding hole in baseplate 403 below chamber 405B, so chamber 405B is isolated. "Loading" in this case refers to the set point sample mass 426A which resides in perforated pipe 422, FIG. 4. The "Loading/Measurement" duration may be about 20 seconds whereas the permeability measurement duration may last 10 to 15 seconds.

Figure 5:
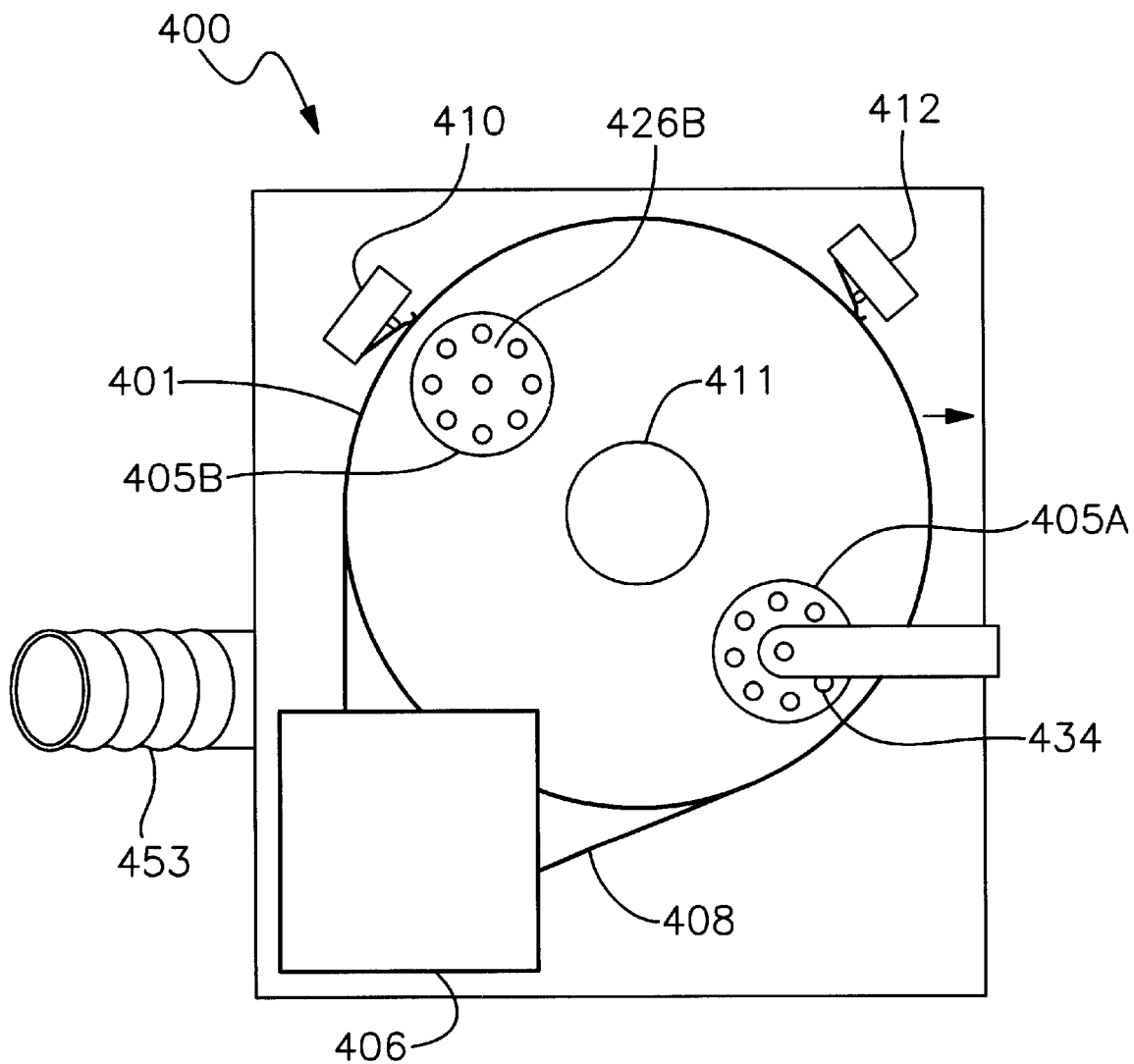
FIG. 5 shows the turntable in its transfer/eject position.

After the turntable 401 reaches the "Transfer/Eject" position seen in FIG. 5, and which position is determined by actuation of microswitch 412, transfer cylinder 430, FIG. 4, drives the set point mass portion 426A of sample 102 up into compression chamber 405B, FIGS. 4 and 5. The top of piston 432 stops just below the bottom of turntable 401, or flush with the top of baseplate 403. Almost simultaneously, compressed air nozzle 434, FIGS. 3 and 5, blows the prior set point mass 426C portion of prior sample 102 out of compression chamber 405A, through a hole in baseplate 403, onto balance 436. The time duration at this "Transfer/Eject" position is only one to two seconds, after which the turntable 401 rotates again to the next "Load/Measure" position, as determined by microswitch 410.

It is important to note that this rotation of two compression chambers permits parallel operations, thus reducing overall testing time.

Figure 3:
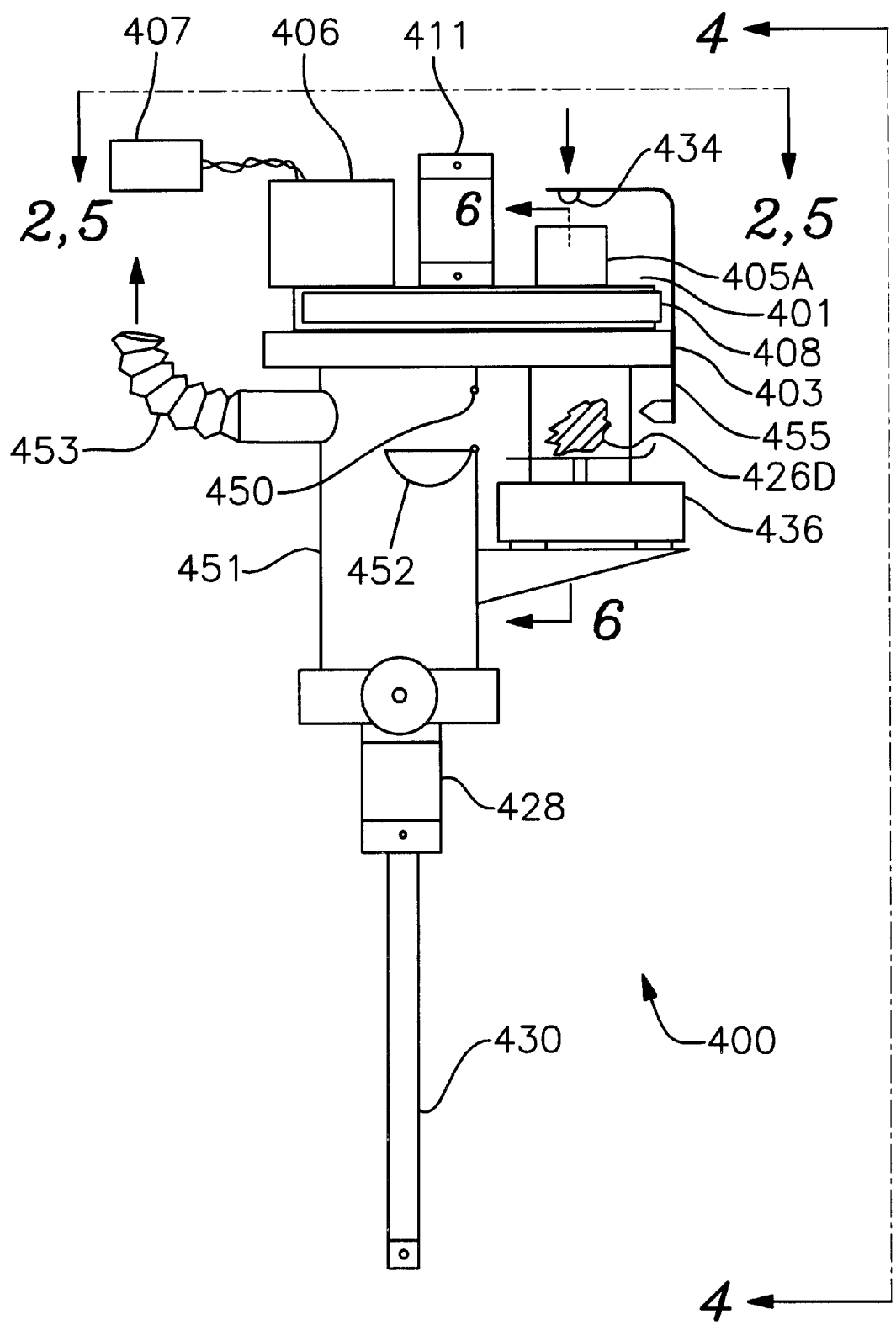
FIG. 3 is a side view.

Before disclosing the continuous compression permeability measurement aspects of the invention, we complete the sample handling by noting in FIG. 3 that the ejected sample 426D, after being automatically weighed by balance 436, is blown into hole 450 in bypass tube 451 by a pulse of compressed air from nozzle 455. Hole 450 is produced when tightly-sealed door 452 is opened by actuator 454 (FIG. 4). Ejected sample 426D then passes via pipe 453 to lint box 130. Balance 436 acquires the precise mass of sample 426D while the permeability of the next sample is being measured and while the sample after that is being loaded, again, in parallel operations involving three successive samples 102. The finished sample 426D is blown into hole 450 during a turntable 401 rotation so that the system suction is not disturbed during loading or measuring operations.

Figure 6:
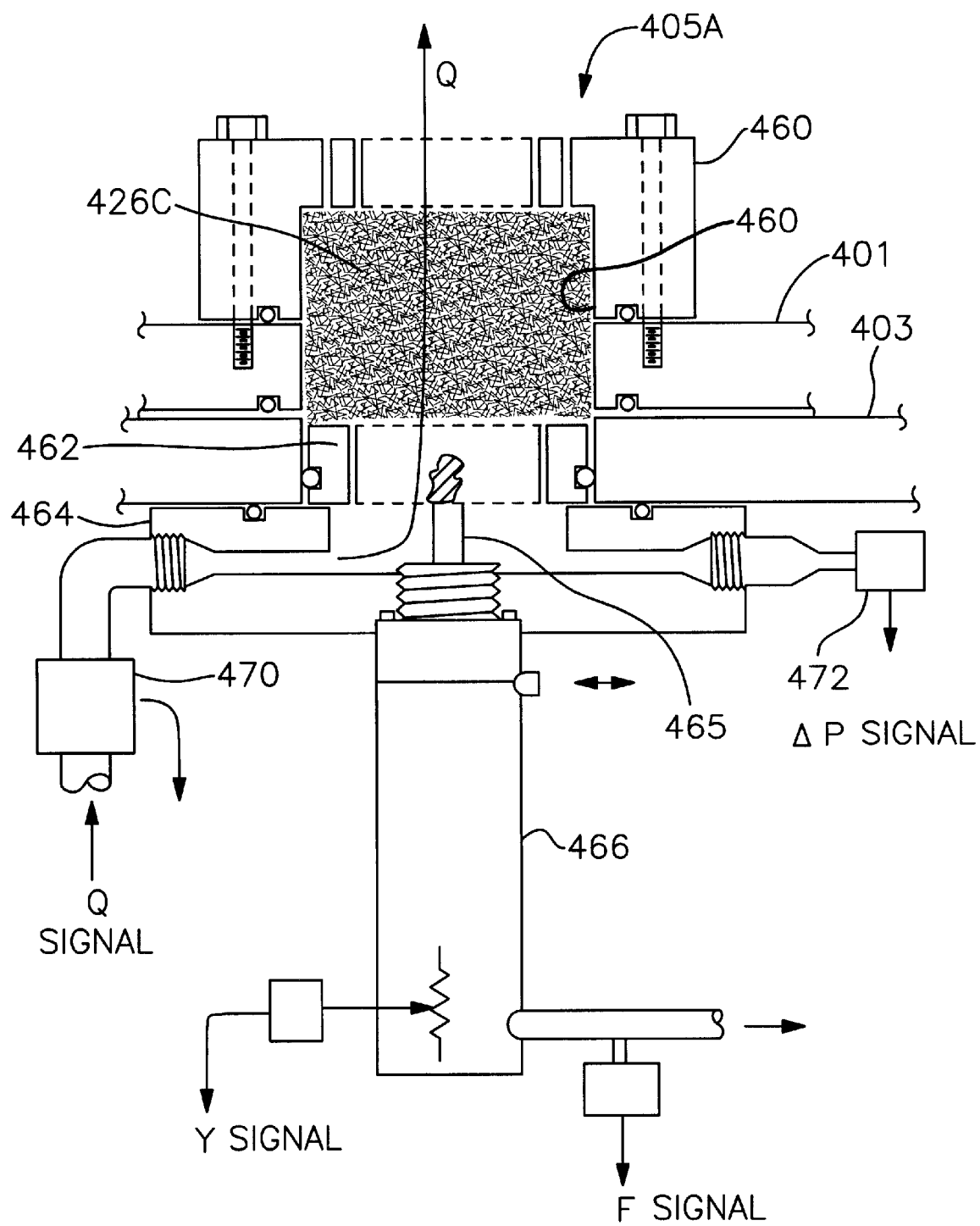
FIG. 6 is a partial cross section taken on line 6—6 of FIG. 3.

FIG. 6 is a cross sectional elevational view whose cut lines are indicated in FIG. 3. Test sample entities 426C are seen in concentric and identical internal diameter cylinder bores 461 in chamber cap 460 and turntable 401. Sample compression piston 462 sits in a similar bore in baseplate 403. These bores are precision-aligned and have diameter of nominally 2.060 inches (5.232 cm).

The samples 426C arrive in this "Measurement" position as follows: In the "Transfer/Eject" position (FIG. 5), the transfer piston 432 in FIG. 4, at its most extended extreme, is at the same flush position with respect to baseplate 403 as the measurement piston 462 in FIG. 6 is in its most retracted extreme. Turntable 401 slightly elevates and rotates, carrying sample 426B across the tops of the two pistons, fully extended piston 432 of FIG. 4 and fully retracted piston 462 of FIG. 6, whose tops are, during the transfer, flush with the top of baseplate 403 or the bottom of turntable 401. Upon reaching the measurement position, the designation of sample changes from 426B to 426C, the latter of which is seen in FIG. 6. Note also in FIG. 6 that compression piston 462 is, at its most retracted position, in a precise position assured by the bottom of piston 462 striking the top of mounting plate 464.

Piston 462 is perforated, also with about 100 holes as in the identical compression chamber tops 405A, 405B. Air flow Q, typically in liters/min, measured by flow sensor 470, is delivered at nearly constant pressure difference $\Delta P$, as measured by sensor 472, typically in inches of water column, and permeates sample 426C in compression chamber bore. As the volume of the sample 426C is reduced, or the compression force on the sample is increased, the air flow permeability of the compressed sample 426C "plug" decreases. Also during the continuous compression, as y decreases from a maximum of about 2 inches (5.08 cm) to a minimum of about 0.5 inch (1.27 cm) over a time duration of about ten seconds, the force on the plug increases, as is measured, approximately, by the force F on the piston in air cylinder 466. (More accurate force measurements, those on the plug itself, which range from about zero to over 200 pounds (90 kilogram-force) force, result from installing force transducer between piston rod 465 and compression piston 462.) Permeability (Q, $\Delta P$) and force measurements are acquired by computer 112 as frequently as desired but, for our purposes, we have found that sampling rates of ten per second are adequate.

What matters in the characterization of air flow through fibrous media is rigorous measurement of the permeability of the sample 426C plug and of sample mass and compression volumes or bulk mass densities, $g/cm^3$. It does not matter whether permeability is measured at constant pressure with variable Q, as described above, or at constant Q and variable delta pressure. By permeability we mean $K=\Delta P/Q^2$. Thus, in most basic terms, the physical responses of air flowing through a fibrous sample 426C are completely described by the sample 426C mass, the volume yA, the compression or bulk density of that known mass in that known volume, and the flow Q through the variably compressed plug 461 and pressure differential $\Delta P$ across it, or strictly, plug permeability $K=\Delta P/Q2$. (Gas composition and temperature and absolute atmospheric pressure are needed only in the most exacting of research-type measurements.) Our apparatus measures all of these parameters plus force F during the continuous compression precisely, accurately and with digital sampling so frequent as to approximate continuous measurement, so the air flow permeability characteristics of the unknown sample are completely described. For emphasis and symbolic simplification, air flow permeabilities K for a wide range of bulk densities are the basic data product of the invention.

Figure 7:
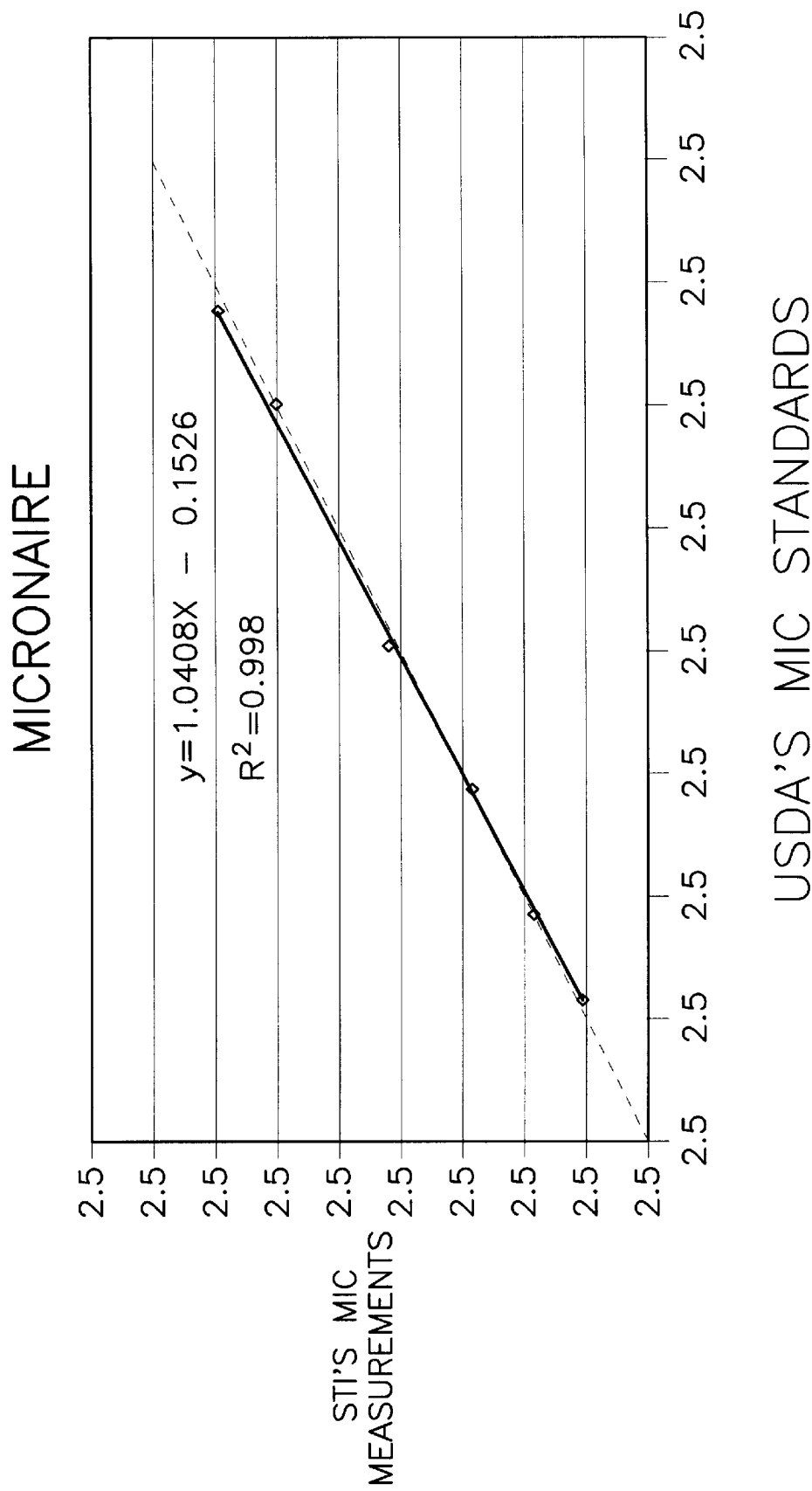
FIG. 7 is a micronaire performance graph.

Thus, FIG. 7 is a performance graph comparing micronaire measurements made employing embodiments of the invention (vertical axis) to USDA micronaire cotton standards. As noted in the Background of the Invention, micronaire is now a dimensionless measurement, since it has been realized that the fineness linear density dimensions in μg/in are incorrect for micronaire.

What is claimed is:

1. An gas flow permeability testing instrument, comprising:
   a testing chamber;
   a device for introducing individualized fibers into a gas flow stream for delivery to said testing chamber;
   sensors in said gas flow stream enabling the determination of fiber mass delivered to said testing chamber;
   a computer connected to said sensors for determining when a predetermined mass set point is reached, and outputting a control signal to terminate delivery of fibers to said testing chamber; and
   a system for testing the permeability of a fiber sample within said testing chamber, and thereafter ejecting the fiber sample.

2. The instrument of claim 1, which further comprises a gravimetric balance for more precisely determining the mass of the fiber sample.

3. The instrument of claim 1, wherein:
   said sensors in said gas flow stream comprise a volumetric flow rate sensor and an electro-optical mass concentration sensor; and wherein
   said computer determines when the predetermined mass set point is reached by integrating over time the product of mass concentration and mass flow rate.

4. The instrument of claim 1, wherein:
   said testing chamber has a movable wall to very the volume thereof; and which further comprises:
   a gas flow system for driving a gas flow through said chamber with at least the gas flow rate and pressure difference measured so as to determine permeability;
   an actuator driving said movable wall in a substantially continuous manner so as to compress the fiber sample and a transducer for measuring position of said movable wall of said chamber; and
   a data processing device for acquiring at least gas flow rate, pressure difference, and position data at a sampling rate while said wall is moving.

5. A method for measuring gas flow permeability, comprising:
   introducing individualized fibers into a gas flow stream for delivery to a testing chamber;
   employing sensors in the gas flow stream enabling the determination of fiber mass delivered to the testing chamber;
   determining when a predetermined mass set point is reached, and terminating the delivery of fibers to the testing chamber;
   testing the permeability of a fiber sample in the testing chamber, and thereafter ejecting the fiber sample.

6. The method of claim 5, which further comprises employing a gravimetric balance to more precisely determine the mass of the ejected fiber sample.

7. The method of claim 5, wherein:
   said step of employing sensors comprises employing a volumetric flow rate sensor and an electro-optical mass concentration sensor; and wherein
   said step of determining when a predetermined mass set point is reached comprises integrating over time the product of mass concentration and mass flow rate.

8. The method of claim 5, wherein said step of testing the permeability of a fiber sample comprises:
   driving a movable wall of the testing chamber in a substantially continuous manner so as to compress the fiber sample while measuring the position of the movable wall and thus the volume of the chamber while measuring gas flow rate and pressure difference so as to determine permeability; and
   acquiring gas flow rate, pressure difference, and position data at a sampling rate while the wall is moving, and calculating micronaire, maturity and fineness based on the acquired data.

\* \* \* \* \*